United States Patent [19]
Smith

[11] Patent Number: 5,744,095
[45] Date of Patent: Apr. 28, 1998

[54] MEDICAL ASSAY CASSETTE

[76] Inventor: Henry J. Smith, 38 Landing, Laguna Niguel, Calif. 92651

[21] Appl. No.: 557,336

[22] Filed: Nov. 14, 1995

[51] Int. Cl.$^6$ .......................... G01N 1/00; G01N 33/543; A61J 1/05

[52] U.S. Cl. ................... 422/58; 422/50; 436/46; 436/518; 604/49; 604/51; 604/272

[58] Field of Search ....................... 128/743, 770, 128/771; 604/48, 49, 51, 93, 264, 272, 403; 606/167, 185; 422/50, 58, 79; 435/287.1, 805, 810; 436/46, 518

[56] References Cited

U.S. PATENT DOCUMENTS 4,627,445  12/1986  Garcia et al. .
5,231,993  8/1993   Haber et al. .
5,279,294  1/1994   Anderson et al. .

*Primary Examiner*—James C. Housel
*Assistant Examiner*—Rodney P. Swartz
*Attorney, Agent, or Firm*—Derrick Michael Reid

[57] ABSTRACT

Over the counter assay cassette for clinical or home use for testing human conditions such as, HIV and Hepatitis B, having a blood well for receiving blood and viewing aperture for viewing an indication of the assay results and a membrane strip disposed within the cassette for receiving the blood and providing an indication of the human condition, is improved with an integrally disposed needle and an outer covering which, in a first position exposes the needle for drawing of the blood and exposes the blood well but covers the viewing aperture, and in a second position, covers the needle and exposes to the viewing aperture, so that, the human can view the results of the assay while the covered needle reduces the risk of secondary inadvertent puncturing by the used needle to reduce the risk of transmission of infectious disease.

10 Claims, 4 Drawing Sheets

MEDICAL ASSAY CASSETTE

FIELD OF THE INVENTION

The present invention relates to the field of clinical assays of biofluids. More particularly, the present invention relates to over the counter assay cassettes for the testing of human conditions.

BACKGROUND OF THE INVENTION

There presently exists over the counter assay cassette for home use for testing of human conditions, such as, pregnancy, ovulation, glucose, HIV, arthritis, and Hepatitis B. These cassettes are typically thin and rectangular in shape typically about 1.25 by 2.5 by 0.25 inches, having a flat top and bottom both thin, about 1/8 inch, in thickness. Secured within the cassette and running length wise is disposed therein a membrane strip about 0.3125 wide by 2.4375 inches long. The membrane strip is used to absorb blood through a circular 0.1875 inch diameter hole in the top of cassette, to react to the blood, and to then display an indication of a human condition through a 0.25 by 1.3125 inch oblong aperture also in the top of cassette. The hole and aperture in the top being aligned with each other and are positioned over the membrane so that blood is absorbed into the membrane and so that the membrane can be viewed through the viewing aperture to reveal to the user an indication, or a lack thereof, of a human condition. Accompanying the cassette is a needle assembly consisting of a needle base for manual manipulation, a cap buttressing the base, a needle having a sharp end covered by the cap and another end secured within the base, and a donut shaped needle stop disposed around the needle exposing the needle end and buttressing the needle base to define a penetrating length of the sharp end of the needle and the depth of puncture. A user removes the caps and sticks the needle into a finger tip to cause blood to flow from the finger. The penetration into the finger is stopped and determined by the placement of the needle stop relative to the end of the sharp end of the needle. The user then positions the finger over the hole and drops blood into the blood well hole so that the membrane strip will then absorb the drops of the blood. After a predetermined amount of time, the membrane strip under the viewing aperture, may or may not reveal an indication of a human condition. Each different type of human condition requires a unique type of membrane. Thus, the cassettes can be adapted for testing many conditions, though each individual cassette is only used once with a subsequent disposal.

These cassettes may be conveniently sold over the counter to individuals or may be used by doctors in clinical or medical offices or may be used by laboratory technicians in laboratories. The cassettes are disposable. The needle and the cassette are to be discarded after only one use. The user should place the cap back over the needle prior to discarding it so that it is not exposed. The user should also take extreme care not to expose the bloody needle to others. However, many potential users may not appreciate and take adequate precaution when handling a bloody needle. The potential dangers associated with discarding bloody needles are serious, especially in view of the significant dangers associated with the transmission of disease, for example, HIV. An exposed bloody needle discarded in waste bins is a potential hazard to janitorial personnel. An exposed bloody needle not properly discarded presents a potential risk of acquiring a disease communicated from an improperly discarded needle. During and after use, the needle may be mishandled or become inadvertently lost, and not properly discarded thereby presenting a potential hazard to others. These and other disadvantages are solved or reduced using the present invention.

SUMMARY OF THE INVENTION

An object of this invention is to prevent or lessen the risk of communicating disease.

Another object of this invention is to provide a cassette and needle assembly which prevents or lessens the risk of communicating disease.

Yet another object of this invention is to provide a cassette and needle assembly for the assay of a human condition while preventing or lessening the risk of communicating disease.

Still another object of the invention is to provide a cassette and needle assembly for the assay of a human condition by blood sampling while preventing or lessening the risk of communicating disease using a covering having at least two positions which in one position exposes the needle for the drawing of the blood and covering the assay result indication, and while in another position covers the needle to expose the assay result indication.

Yet a further object of the present invention is to provide a cassette and needle assembly for the assay of a human condition by blood sampling while preventing or lessening the risk of communicating disease using a covering having at least two positions which in one position exposes the needle for the drawing of the blood and covering the assay result indication, and while in another position covers the needle to expose the assay result indication, so that the user will be required to cover the needle in order to view the assay result indication.

The present invention is a substantial improvement and modification of existing clinical assay cassettes for home use for testing of human conditions, such as, glucose, HIV, and Hepatitis B, among others. The thin rectangular cassettes having an internal membrane strip exposed by an oblong viewing aperture and circular blood hole well, are modified to further integrally include an internally disposed needle and an external covering means. The covering means, which may be preferably an outer sleeve has a first position to enable exposure of the sharp needle end for puncturing a finger of a user for drawing blood drops and to cover the viewing aperture for preventing the user to see the result of the assay when the needle is so exposed, and has a second position to disable exposure of the sharp needle for preventing the communication of disease and to expose the viewing aperture to reveal an indication of the result of the assay. In practice, the covering means is in a first position, and the user manipulates the cassette assembly to expose the needle and puncture the finger tip. The user then drops blood drops into the blood well. The user then manipulates the covering means to expose the viewing aperture in order to see the indication of the result of assay. When the user manipulates the covering means to expose the viewing aperture, the covering means simultaneously covers the needle end so that it is no longer exposed. This process insures that during normal use of the improved cassette, the user will, knowingly or unknowingly, cover the exposed needle to lessen the risk that another may be inadvertently pricked by the needle.

In the preferred forms of the invention, the covering means is a sleeve which moves along the length of the cassette, from a middle first position covering the viewing aperture to an end second position covering the needle. The needle is assembled within the cassette, so that when the cassette is discarded, the needle is also discarded, and when the assay is viewed by the user, the needle will be automatically covered which then lessens the risk of accidental exposure of the bloody needle end to others. The needle is preferably integral to a needle assembly. Preferably, the needle assembly may be a stationary assembly within the cassette having an aperture into which extends the needle tip and into which is forced a finger. Preferably, the needle assembly may also be a slidable plunger assembly having a distal button end which is pressed by the user forcing the needle end to extend outside the assembly for exposure to the finger. The needle assembly preferably has a donut shaped needle stop disposed around the needle exposing the needle end and buttressing the needle base to define a penetrating length of the sharp end of the needle. The needle assembly preferably has a needle cap. A user removes the cap and sticks the needle into a finger tip to cause blood to flow from the finger.

After the assay has been indicated, the user simply discards the cassette with the needle covered thereby protecting others from inadvertent exposure to the bloody end. The advantage of the integral needle assay cassette is the required covering of the needle when viewing the results through the viewing aperture after the sleeve has been moved into its second position. The required and automatic covering of the needle lessen the risk of inadvertent exposure of the needle and the inadvertent communication of harmful diseases. These and other advantages will become more apparent from the following detailed description of the preferred embodiment.

DETAILED DESCRIPTION OF THE PREFERRED EMBODIMENT

Figure 1A:
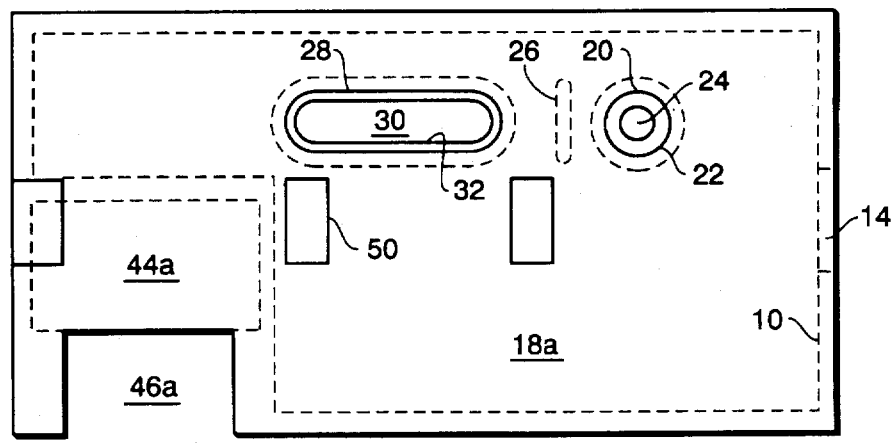
FIG. 1a is a top view of a top portion of an assay cassette with a needle end aperture.

An embodiment of the present invention is described with reference to the figures using reference designations as shown in the figures. Referring to FIGS. 1a through 2d, an improved stationary needle assay cassette is shown as preferably having a cassette top shown in FIGS. 1a and 1b, and a cassette bottom shown in FIGS. 1c and 1d. The cassette top has a downwardly extending top flange 10 and the cassette bottom has an upwardly extending bottom flange 12. When the cassette top and bottom are joined together by alignment of a downwardly extending top alignment tab 14 into a bottom notch 16 in the bottom flange 12, the top flange 10 and the bottom flange 12 buttress each other forming an internal cavity 18ab consisting of a top cavity portion 18a and bottom cavity portion 18b. Proximal to the flange 10 are fitting pins, not shown, and proximal to flange 12 are fitting holes, also not shown, which fittings pins are in respective alignment with the fitting holes, so that the top and bottom of the cassette snaps together.

Figure 1B:
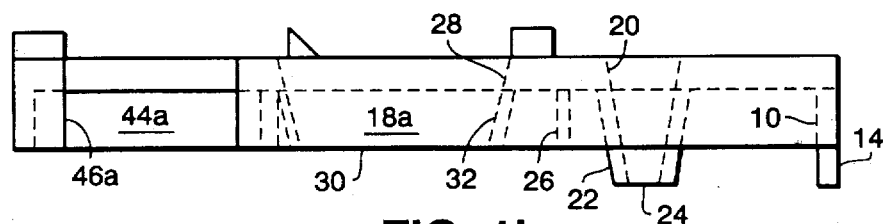
FIG. 1b is a side view of the top portion of the assay cassette with the needle end aperture.

The cassette top of FIGS. 1a and 1b includes a circular blood well 20 consisting of a downwardly extending circular flange 22 forming a blood hole 24, a downwardly extending membrane flange 26, an oblong shaped viewing aperture 28 consisting of an oblong hole 30 defined by an oblong flange 32. The cassette bottom of FIGS. 1c and 1d includes upwardly extending membrane guides 33a, 33b and 33c, and includes a rectangular membrane cavity 34abc with a first end portion 34a, with a middle raised portion 34b and with second end portion 34c. In practice, a thin membrane strip 36 is disposed within and extends the length and width the membrane cavity 34abc while being held in alignment by membrane guides 33. When the top and bottom of the cassette are joined together, the raised portion 34b of the membrane cavity 34abc presses against the center of the membrane strip 36 then being centered and pressed against the viewing aperture flange 32, while an end portion of the strip 36 is in alignment with and pressed downwardly by the blood aperture flange 22 into membrane cavity portion 34c. The membrane flange 26 deters blood dropped into the well 20 from flowing over the membrane 36 into the viewing hole 30, so that blood serum must propagate through the membrane 36 which then provides an indication of human condition. All of these elements and functions are common to prior art assay cassettes.

Figure 2A:
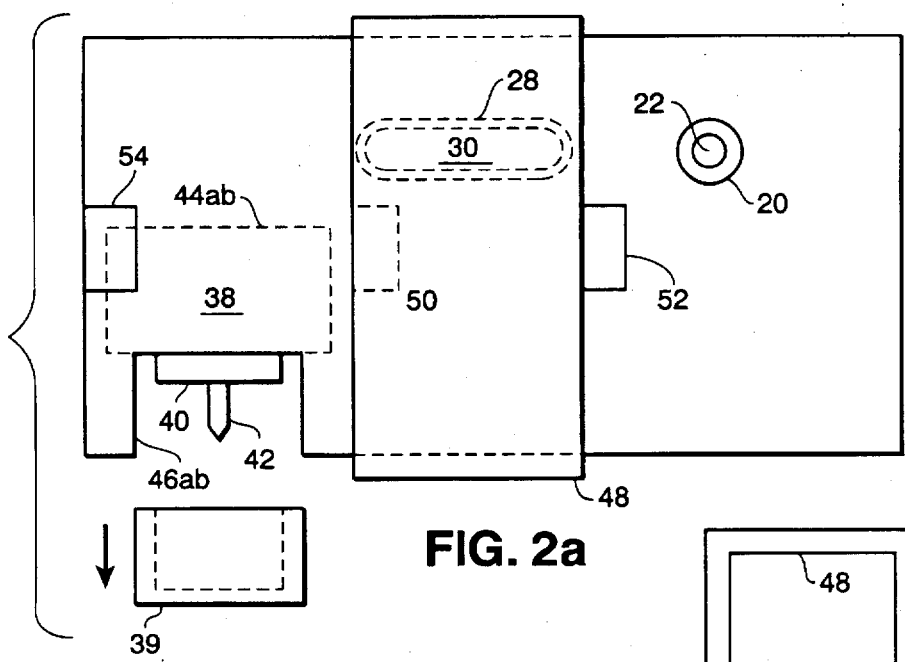
FIG. 2a is a top view the assay cassette having a sleeve in a first position exposing the needle end aperture
Figure 2B:
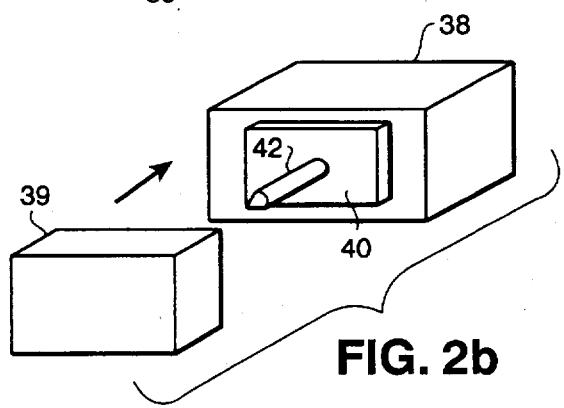
FIG. 2b is an isometric view of a stationary needle assembly.

The cassette is improved to receive, in the preferred form, a stationary needle assembly shown in FIG. 2b, including box shaped needle base 38, a needle cap 39, a flat rectangular needle stop 40 and a needle 42. The needle 42 extends through the stop 40 and is securely fixed with the base 38. The needle stop 40 defines the length of the needle 42 which extends from the stop 40 to define the maximum penetration into a human finger when used to draw blood. The cap 39 serves to protect against inadvertent punctures and maintenance of needle sterilization upon manufacture of the needle assembly of FIG. 2b. The cap 39 can be manually fitted onto the base 38 by friction fitting around the stop 40. The human may place the cap 39 back over the needle 42 and stop 40 after puncturing a finger.

Figure 1C:
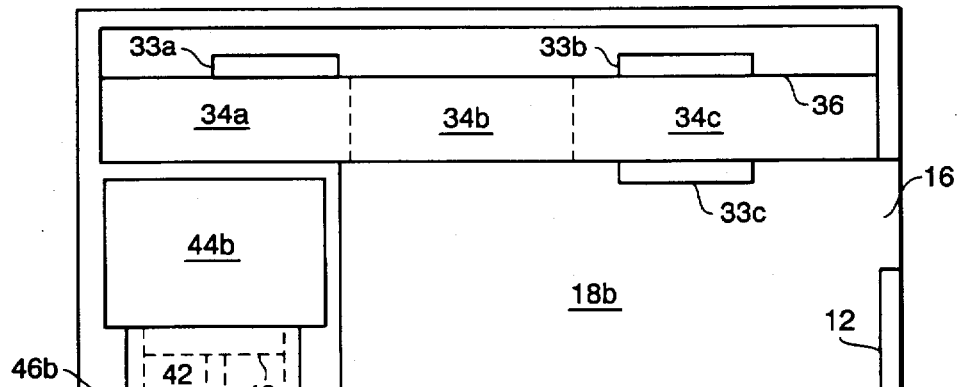
FIG. 1c is a top view of a bottom portion of the assay cassette having a stationary needle cavity and the needle end aperture.
Figure 1D:
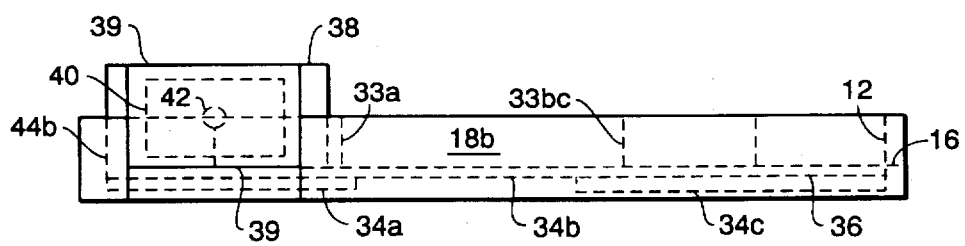
FIG. 1d is a side view of the bottom portion of the assay cassette having a stationary needle cavity and the needle end aperture.

The cassette top of FIGS. 1a and 1b has a partial needle assembly cavity 44a and the cassette bottom of FIGS. 1c and 1d has another partial assembly cavity 44b which are aligned and combined into a needle assembly cavity 44ab into which is disposed the needle assembly base 38. The cassette top of FIGS. 1a and 1b has a partial puncturing aperture 46a and the cassette bottom of FIGS. 1c and 1d has another partial puncturing aperture 46b which are aligned and combined into a puncturing aperture 46ab into which extends the stop 40 and needle 42 both covered by the cap 39.

Figure 2C:
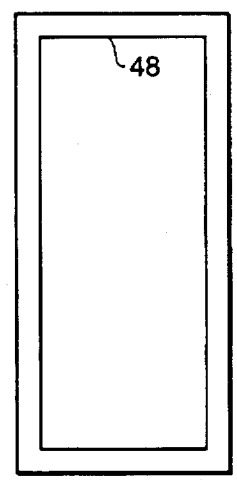
FIG. 2c is a side view of the sleeve.
Figure 2D:
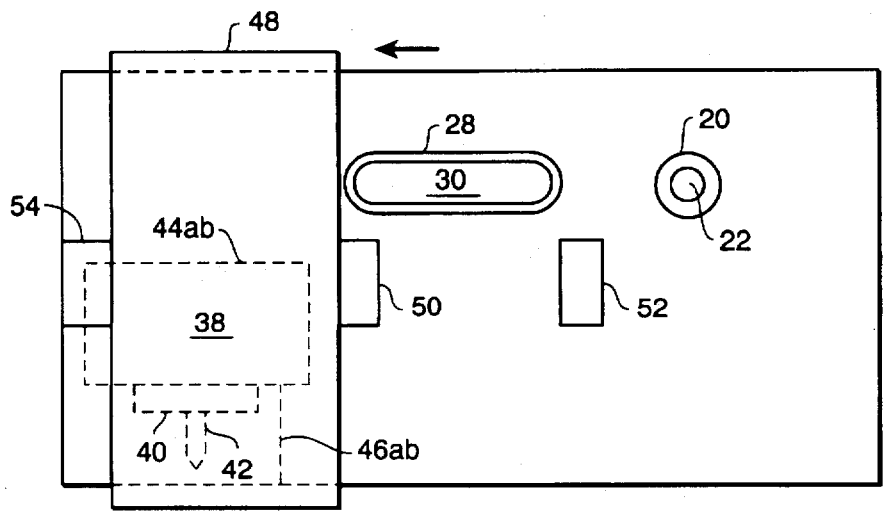
FIG. 2d is a top view the assay cassette having the sleeve in a second position covering the needle end aperture.

During manufacture, the needle assembly 38, 39, 40 and 42 is positioned within the cavity 44ab and aperture 46ab when the top and bottom cassette are fitted together using alignment tab 14 fitting into notch 16, and using the fitting pins and fitting holes, both not shown. A rectangular sleeve 48, shown in FIG. 2c is adapted in size to fit around the cassette. A triangular friction post 50 on the exterior of the top of the cassette exerts a frictional force against the sleeve 48 to secure the sleeve 48 into a first of two positions, a first position defined by a first stop post 52 and a second stop post 54. In the first position, the sleeve 48 is secured by friction post 50 when the sleeve 48 is stopped by the first post 52. In the second position, the sleeve 48 is stopped between and by both the friction post 50 and the second stop post 54. As may now be apparent, the sleeve 48 in the first position covers the viewing aperture 30 while exposing the puncturing aperture 46ab so that a human may firstly remove the needle cap 39 and press a finger against the needle 42 to draw the blood from the finger which forms drops that the human can drop into the blood well 20. After puncturing a finger, the human may then manually slide the sleeve 48 to the second position which covers the needle 42 from exposure and inadvertent puncturing while exposing the view aperture 30. In this manner, the human user covers the needle 42 when obtaining a visual indication of the assay through the viewing aperture 30.

Figure 3A:
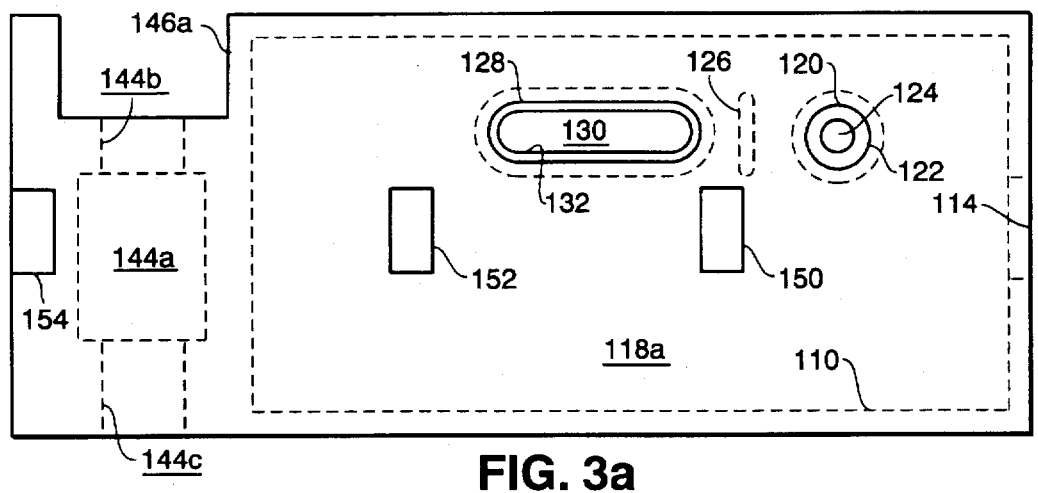
FIG. 3a is a top view of a top portion of an assay cassette with a needle plunger aperture.
Figure 3B:
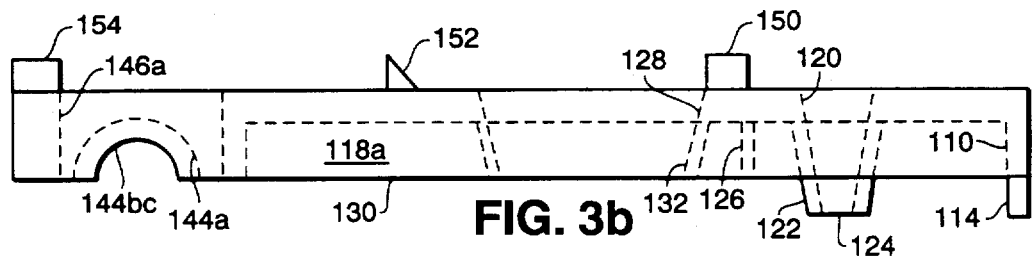
FIG. 3b is a side view of the top portion of the assay cassette with the needle plunger aperture.
Figure 3C:
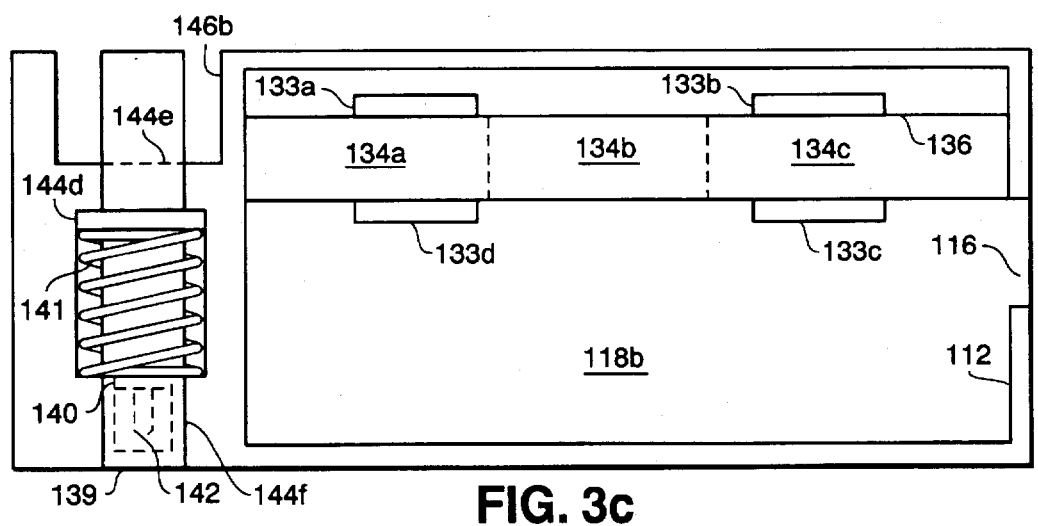
FIG. 3c is a top view of a bottom portion of the assay cassette having a plunger needle cavity and the needle plunger aperture.
Figure 3D:
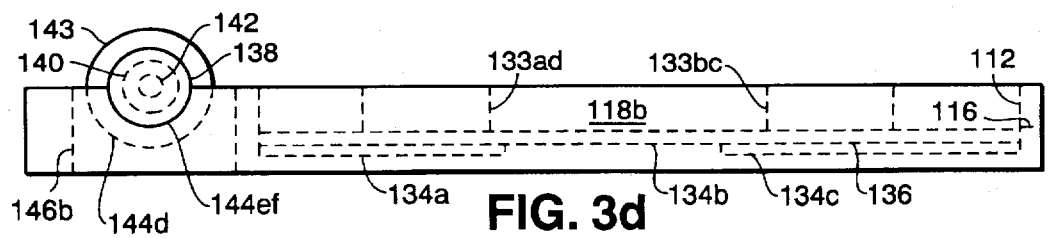
FIG. 3d is a side view of the bottom portion of the assay cassette having the needle plunger cavity and the needle end aperture.

Referring to FIGS. 3a through 4d, another improved plunger needle assay cassette is shown as preferably having a cassette top shown in FIGS. 3a and 3b, and a cassette bottom shown in FIGS. 3c and 3d. The cassette top has a downwardly extending top flange 110 and the cassette bottom has an upwardly extending bottom flange 112. When the cassette top and bottom are joined together by alignment of a downwardly extending top alignment tab 114 into a bottom notch 116 in the bottom flange 112, the top flange 110 and the bottom flange 112 buttress each other forming an internal cavity 118ab consisting of a top cavity portion 118a and bottom cavity portion 118b. Proximal to the flange 110 are fitting pins, not shown, and proximal to flange 112 are fitting holes, also not shown, which fittings pins are in respective alignment with the fitting holes, so that the top and bottom of the cassette snaps together.

The cassette top of FIGS. 3a and 3b includes a circular blood well 120 consisting of a downwardly extending circular flange 122 forming a blood hole 124, a downwardly extending membrane flange 126, an oblong shaped viewing aperture 128 consisting of an oblong hole 130 defined by an oblong flange 132. The cassette bottom of FIGS. 3c and 3d includes upwardly extending membrane guides 133a, 133b, 133c and 133d and includes a rectangular membrane cavity 134abc with a first end portion 134a, with a middle raised portion 134b and with second end portion 134c. In practice, a thin membrane strip 136 is disposed within and extends the length and width of the membrane cavity 134abc while being held in alignment by membrane guides 133. When the top and bottom of the cassette are joined together, the raised portion 134b of the membrane cavity 134abc presses against the center of the membrane strip 136 then being centered and pressed against the viewing aperture flange 132, while an end portion of the strip 136 is in alignment with and pressed downwardly by the blood aperture flange 122 into membrane cavity portion 134c. The membrane flange 126 deters blood dropped into the well 120 from flowing over the membrane 136 into the viewing aperture 130, so that blood serum must propagate through the membrane 136 which then provides an indication of human condition. These elements and functions are also common to prior art assay cassettes and are identical to cassette of FIGS. 1a through 2d.

Figure 4A:
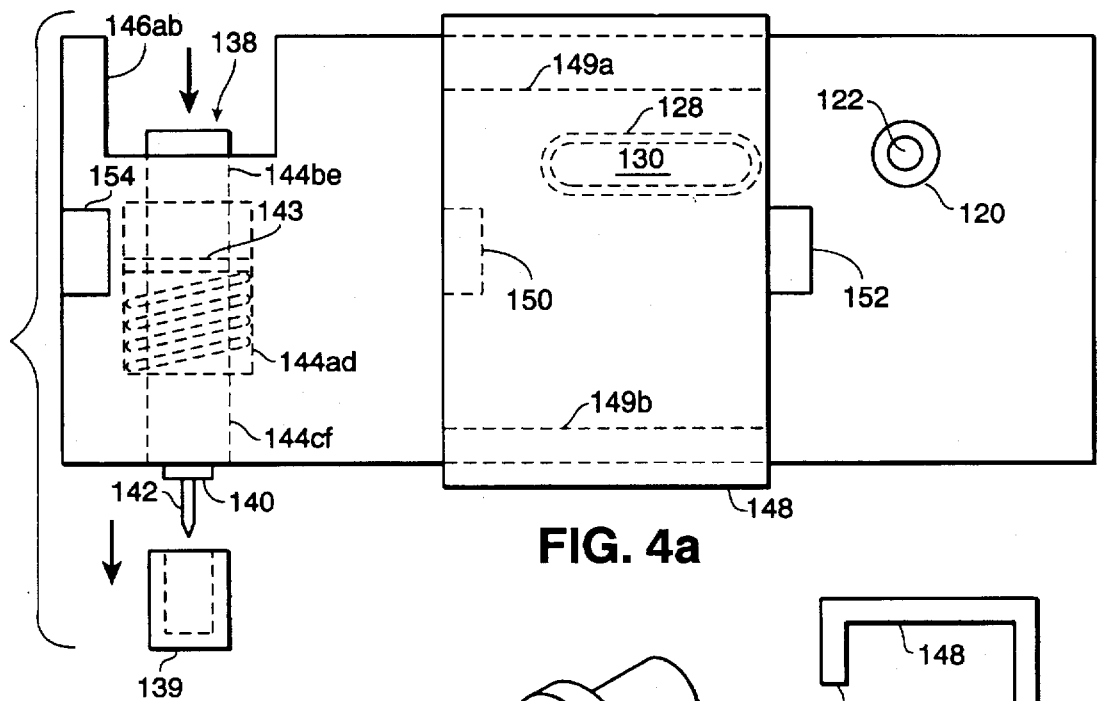
FIG. 4a is a top view the assay cassette having a cover in a first position exposing the needle plunger aperture.
Figure 4B:
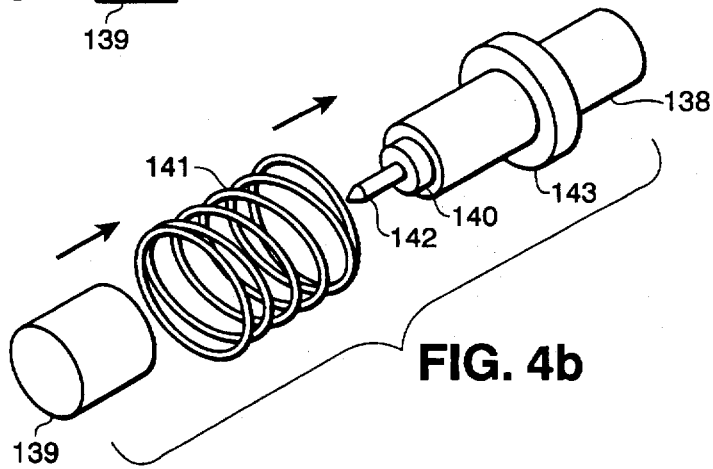
FIG. 4b is an isometric view of a needle plunger assembly.
Figure 4C:
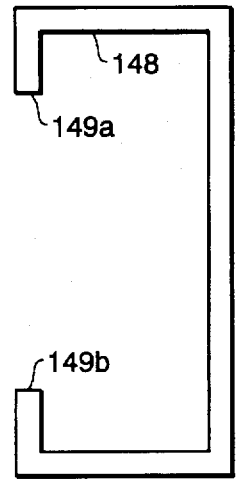
FIG. 4c is a side view of the cover.

The cassette of FIGS. 3abcd and 4abcd is also improved to received, in another preferred form, a plunger needle assembly shown in FIG. 4b, including a cylindrically shaped needle base 138, circular needle cap 139, a circular needle stop 140, a spring 141, a needle 142 and a ring flange 143. The ring flange 143 is preferably made integrally with the base 138. The needle 142 extends through the stop 140 and is securely fixed with the base 138. The spring 141 fits around the base 138 extending from the ring 143 flange towards the stop 140. The needle stop 140 defines the length of the needle 142 which extends from the stop 140 to define the maximum penetration into a human finger when used to draw blood. The cap 139 serves to protect against inadvertent punctures and maintenance of needle sterilization upon manufacture of the needle assembly of FIG. 4b. The cap 139 can be manually fitted onto the base 139 by friction fitting around the stop 140.

Figure 4D:
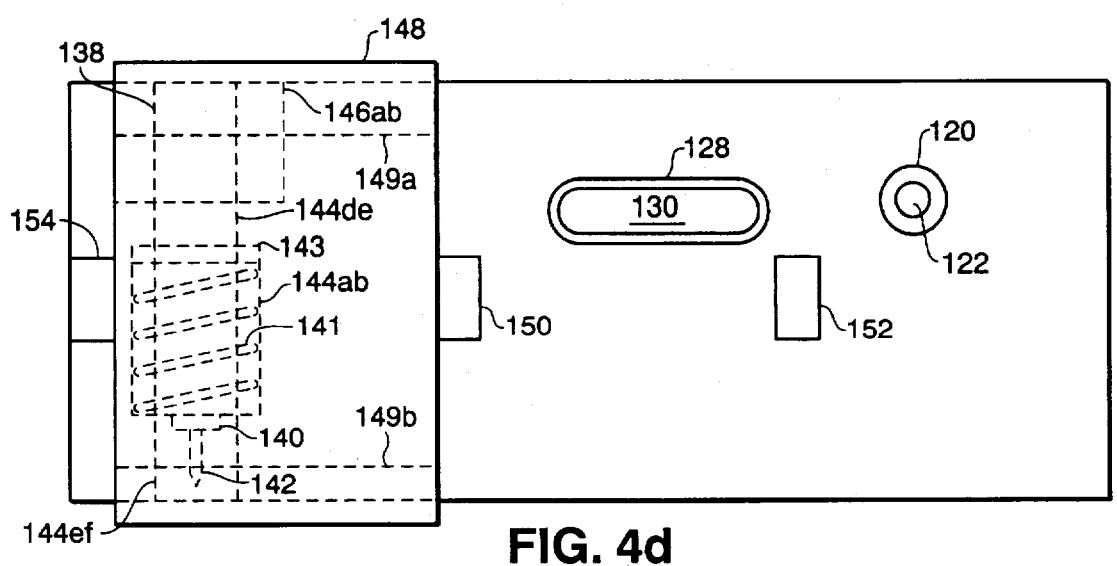
FIG. 4d is a top view the assay cassette having the cover in a second position covering the needle plunger aperture.

The cassette top of FIGS. 3a and 3b has a partial needle assembly cavity having portions 144a, 144b and 144c and the cassette bottom of FIGS. 3c and 3d has another partial assembly cavity having portions 144d and 144e and 144f. The cavity portions 144a, 144b and 144c are respectively aligned to cavity portions 144d, 144e and 144f, all of which combined into a needle assembly cavity having combined portions 144ad, 144be and 144cf into which is disposed the needle assembly 138–143. The cassette top of FIGS. 3a and 3b has a partial plunging aperture 146a and the cassette bottom of FIGS. 3c and 3d has another partial plunging aperture 146b which are aligned and combined into a plunging aperture 146ab into which extends a distal end of the plunger base 138 as shown in FIG. 3c. In a resting position, the cap 139, needle 142 and stop 140 are disposed into partial cavity 144cf, the spring 141 around a proximal end of the base 138 and the ring flange 143 are disposed in partial cavity 144ad, and a distal end of the base 138 is disposed in the partial cavity 144be and extending into plunging aperture 146ab as shown in FIGS. 3c, 3d and 4d. In a plunging position, the spring 141 is compressed to move the base 138 then positioned so that the stop 140 and needle 142 are exposed as shown in FIG. 4a.

During manufacture, the needle assembly 138–143 is positioned within the cavity 144abcdef and aperture 146ab when the top and bottom cassette are fitted together using alignment tab 114 fitting into notch 116, and using the fitting pins and fitting holes, both not shown. A flanged rectangular sleeve 148, is adapted in size to fit around the cassette secured by flanges 149a and 149b of the sleeve 148 shown in FIG. 4c. A triangular friction post 150 on the exterior of the top of the cassette exerts a frictional force against the sleeve 148 to secure the sleeve 148 into a first of two positions, a first position defined by a first stop post 152 and a second stop post 154. In the first position, the sleeve 148 is secured by friction post 150 when the sleeve 148 is stopped by the first post 152. In the second position, the sleeve 148 is stopped between and by both the friction post 150 and the second stop post 154. Until the sleeve 148 is moved to the second position, the post 150 provides friction resistance against sleeve movement. As may now be apparent, the sleeve 148 in the first position covers the viewing aperture 130 while exposing the plunging aperture 146ab so that a human may firstly press against the distal end of the base 138 in the aperture 146ab to expose the needle cap 139 on the opposite side of the cassette as shown in FIG. 4a to move the plunging assembly 138–143 from the resting position to the plunging position. In the plunging position, a human may then remove the cap 139 to expose the needle 142 and stop 140. The human then presses a finger against the needle 142 to draw the blood from the finger which forms drops that the human can drop into the blood well 120. After puncturing the finger, the human discontinues pressing the distal end of the base 138 in the plunging aperture 146ab so that the spring 141 moves the needle assembly 138–143 back to the resting position. The human may then place the cap 139 back onto the base 138 around the needle 142 and stop 140 prior to releasing the spring loaded plunger base 138. After puncturing a finger, the human may then manually slide the sleeve 148 to the second position which covers the needle 142 from exposure and inadvertent puncturing while exposing the view aperture 130. In this manner, the human user covers the needle 142 when obtaining a visual indication of the assay through viewing aperture 130.

The above two preferred embodiments are mere examples of the invention, which includes an improved assay cassette having a self contained needle and a cover means having two positions, the first of which enables exposure of a needle for drawing blood which is then dropped into a blood well and a second position revealing the viewing aperture while covering the used needle, so that, precaution is taken against risks for secondary inadvertent puncturing of human tissue by an uncovered needle after use. Those skilled in the art may make many enhancements, improvements and modifications, however, those enhancements, improvements and modifications may nonetheless fall within the spirit and scope of the following claims.

What is claimed is:

1. A cassette for assaying a human condition comprising a casing defining a cavity within said cassette, a viewing aperture disposed in said casing and extending to said cavity for viewing an indication of said human condition of a human, a blood well disposed in said casing and extending to said cavity for receiving human blood to be assayed, an assay membrane disposed in said cavity for absorbing said human blood through the blood well and providing said indication, said human blood diffuses from said blood well through said assay membrane towards said viewing aperture, wherein improvement comprises,
    a needle for puncturing said human to draw said human blood, said needle disposed in said cavity and extending outwardly through said casing of said cassette, said needle having a base end secured within said casing and having a needle end extending outwardly from said casing of said cassette for puncturing said human, and
    a covering means mounted onto said cassette, said covering means having a first cover position for exposing said needle end while covering said viewing aperture and a second cover position for covering said needle end while exposing said viewing aperture.

2. The cassette of claim 1 wherein, said casing having a side and a face, said covering means is a sleeve having an covering aperture through which is disposed said cassette, said improvement further comprising,
    a first stop means disposed on said face for positioning said sleeve in said first cover position for exposing said needle end at said side, for exposing said blood well on said face, and for covering said viewing aperture on said face, and
    a second stop means disposed on said face for positioning said sleeve in said second cover position for covering said needle end at said side, for covering said blood well on said face, and for exposing said viewing aperture on said face.

3. The cassette of claim 1 wherein said improvement further comprises,
    a needle aperture within said casing of said cassette for receiving a human finger of said human, said needle end extending into said needle aperture for puncturing said human finger to draw said human blood when said human finger is received and pressed into said needle aperture.

4. The cassette of claim 1 wherein said improvement further comprises,
    a needle aperture within casing of said cassette for receiving a human finger of said human, said needle end extending into said needle aperture for puncturing said human finger to draw said human blood when said human finger is received and pressed into said needle aperture, and
    a cap disposed within said needle aperture for covering said needle end prior to puncturing said human finger.

5. The cassette of claim 1 wherein said casing comprises a top and bottom fitted together to define said cavity, said improvement further comprises,
    a needle base disposed within said cavity between said top and bottom of said casing, said needle integrally formed in said needle base at said base end, said needle extending from said needle base,
    a needle stop disposed around said needle end and exposing a needle tip of said needle end, said needle stop buttressing said needle base, said needle stop defining a depth of puncture by said needle tip,
    a needle aperture within said top and bottom of said casing of said cassette for receiving a human finger, said needle tip for puncturing at said depth said human finger to draw said human blood, and
    a cap disposed within said needle aperture for covering said needle tip extending into said needle aperture for preventing puncturing of said human finger when said cassette is not in use.

6. The cassette of claim 1 wherein, said casing comprises a top and bottom fitted together to define said cavity, said improvement further comprises,
    a needle base disposed within said cavity between said top and bottom of said casing, said cavity for positioning said needle base in a first needle position or a second needle position, said needle integrally formed in said needle base at said base end, said needle extending from said base end of said needle base, said needle end disposed within said cavity when said needle base is in said first needle position, said needle end exposed outside of said cavity for puncturing a first human finger to draw said human blood when said needle base is in said second needle position, and
    a plunger aperture within said top and bottom of said casing of said cassette for receiving a second human finger and for exposing said base end of said needle base when said needle base is in said first needle position, said plunger aperture for receiving said second human finger for pressing against said base end of the needle base for moving said needle base from said first needle position to said second needle position for exposing said needle end.

7. The cassette of claim 6 wherein said casing has a side and a face, said covering means is a cover for covering said side and face of said cassette, said improvement further comprising, a first stop means disposed on said face for positioning said cover in said first cover position for exposing said needle end extending outwardly from said side of said cassette, for exposing said blood well disposed on said face, and for covering said viewing aperture disposed on said face, a second stop means disposed on said face for positioning said cover in said second cover position for covering said needle end, for covering said blood well, and for exposing said viewing aperture, and a friction means disposed on said face and buttressing said cover, said friction means is disposed between said first and second stop means to resist movement of said cover from said first cover position to said second cover position.

8. The cassette of claim 1 wherein said casing comprises a top and bottom fitted together to define said cavity, said improvement further comprises, a needle base disposed within said cavity between said top and bottom of said casing, said cavity for positioning said needle base in a first needle position or a second needle position, said needle integrally formed in said needle base at said base end, said needle extending from said base end of said needle base, said needle end disposed within said cavity when said needle base is in said first needle position, said needle end exposed outside of said cavity for puncturing a first human finger to draw said blood when said needle base is in said second needle position, and a spring means disposed within said cavity and buttressing said needle base and said cavity of said casing for spring action between said cavity and said needle base for spring loading said needle base to said first needle position and for resisting movement of said needle base to said second needle position, and a plunger aperture within said top and bottom of said casing of said cassette for receiving a second human finger and for exposing said base end of said needle base when said needle base is in said first needle position, said plunger aperture for receiving said second finger for pressing against said base end of said needle base for compressing said spring and moving said needle base from said first needle position to said second needle position.

9. The cassette of claim 8 wherein said improvement further comprises, a needle aperture within said casing of said cassette for receiving a human finger of said human, said needle end extending into said needle aperture for puncturing said human finger to draw said human blood when said human finger is received and pressed into said needle aperture, and a cap disposed within said needle aperture for covering said needle end prior to puncturing said first human finger.

10. The cassette of claim 8 wherein said improvement further comprises, a needle stop disposed around said needle end and exposing a needle tip of said needle end, said needle stop buttressing said needle base, said needle stop defining a depth of puncture of said first human finger by said needle tip.

* * * * *